United States Patent [19]

Blacker et al.

[11] Patent Number: 5,912,355

[45] Date of Patent: Jun. 15, 1999

[54] CHIRAL SYNTHESIS OF TERTIARY ALCOHOLS WITH A HYDROLASE

[75] Inventors: Andrew John Blacker, Leeds; Andrew George Brewster; Robert Jeffrey Copeland, both of Macclesfield; Robert Antony Holt, Northallerton, all of United Kingdom

[73] Assignees: Zeneca Limited, London, United Kingdom; Mochida Pharmaceutical Co., Ltd., Tokyo, Japan

[21] Appl. No.: 08/968,510

[22] Filed: Nov. 12, 1997

Related U.S. Application Data

[62] Division of application No. 08/535,134, filed as application No. PCT/GB94/00793, Apr. 15, 1994, Pat. No. 5,854,062.

[30] Foreign Application Priority Data

Apr. 16, 1993 [GB] United Kingdom ............... 9307924

[51] Int. Cl.$^6$ ............... C07D 249/08; C07D 249/10; C07D 249/12; C07D 249/14
[52] U.S. Cl. ................... 548/268.6; 548/263.2; 548/263.4; 548/263.8; 548/264.2; 548/264.8; 548/265.2; 548/265.6; 548/266.8; 548/267.2; 548/267.4; 548/269.4
[58] Field of Search ............... 548/263.2, 263.4, 548/263.8, 264.2, 264.8, 265.2, 265.6, 266.8, 267.2, 267.4, 268.6, 269.4

[56] References Cited

U.S. PATENT DOCUMENTS

| 4,663,463 | 5/1987 | Kung et al. ............... 548/262 |
| 5,166,062 | 11/1992 | Murrow et al. . |
| 5,493,063 | 2/1996 | Takahashi et al. . |

FOREIGN PATENT DOCUMENTS

| 0015756 | 9/1980 | European Pat. Off. . |
| 0044605 | 1/1982 | European Pat. Off. . |
| 047594 | 3/1982 | European Pat. Off. . |
| 061835 | 10/1982 | European Pat. Off. . |
| 094167 | 11/1983 | European Pat. Off. . |
| 0131684 | 1/1985 | European Pat. Off. . |
| 472392 | 2/1992 | European Pat. Off. . |
| 474250 | 3/1992 | European Pat. Off. . |
| 1529818 | 10/1978 | United Kingdom . |
| 2064520 | 6/1981 | United Kingdom . |
| 2 099 818 | 12/1982 | United Kingdom . |

OTHER PUBLICATIONS

Bianchi et al., Chemoenzymatic Synthesis and Biologidal Activity of Both Enantiomeric Forms of Tetraconazole, a New Antifungal Triazole, J. Agric. Food, Chem., 1991, 39, pp. 197–201.

Bianchi, et al., Enzymatic preparation of optically active fungicide intermediates in aqueous and in organic media, Pure & Appl. Chem., 1992, vol. 64, pp. 1073–1078.

Derwent and on–line abstracts, Sagami, Japanese Patent Application 56–048888 (1981).

Janssen et al., PPL–Catalyzed Resolution of 1,2–and 1,3–Diols in Methyl Propionate as Solvent, an Application of the Tandem Use of Enzymes, Tetahedron, 1991, vol. 47, pp. 7409–7416.

*Primary Examiner*—Patricia L. Morris
*Attorney, Agent, or Firm*—Cushman Darby & Cushman Intellectual Property Group of Pillsbury Madison & Sutro, LLP

[57] ABSTRACT

Method of preparing an optically active compound of formula, wherein R and $R^1$ are independently alkyl, alkenyl, alkynyl, alkoxy, alkoxyalkyl, cycloalkyl, aryl, aralkyl, a heterocyclic group or a $C_1$–$C_4$ alkyl-heterocycle, each being optionally substituted, procided that R and $R^1$ are not identical and * is an optically active chiral center, from the corresponding racemic ester or diol by treating with a hydrolase enzyme.

10 Claims, No Drawings

CHIRAL SYNTHESIS OF TERTIARY ALCOHOLS WITH A HYDROLASE

This is a division of application Ser. No. 08/535,134, now U.S. Pat. No. 5,854,062, filed Dec. 11, 1995 which is the national stage application of PCT/GB94/00793 filed Apr. 15, 1994.

This invention relates to a method of chiral resolution of tertiary alcohols and to novel compounds useful in the method.

Certain tertiary alcohols are useful compounds in pharmaceutical and agrochemical outlets, for example, the compounds disclosed in GB 1529818, EP-B-15756, EP-B-44605, EP-B-61835, EP-B-131684, EP-A47594, GB 2064520 and EPA-472392. These compounds usually have an optically active chiral centre and resolution of the compounds can lead to benefits for example, greater activity or lower toxicity with one of the optically active isomers.

European patent application EPA-472392 discloses the compound (+)-2-(2,4-difluorophenyl)-1-[3-[(E)-4-(2,2,3,3-tetrafluoropropoxy)styryl]-1H-1,2,4-triazol-1-yl)-3-(1H-1,2,4-triazol-1-yl)propan-2-ol, which has antifungal activity, and is valuable in treatment of fungal infections in man and in other animals. Intermediates for the preparation of the compound are also disclosed.

EPA-472392 discloses two methods for the preparation of an optically active epoxide of formula (A)

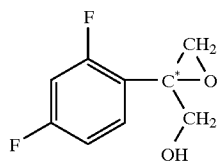

(A)

The first method is a chemical synthesis as demonstrated by processes 1 to 4 of EPA-472392. Process 4 is an asymmetric oxidation process of 2-(2,4-difluorophenyl)allyl alcohol with t-butyl hydroperoxide in organic solvents such as methylene chloride in the presence of a titanium tetraalkoxide such as titanium tetraisopropoxide or titanium tetrabutoxide and of a dialkyl-tartrate.

The second method is demonstrated by processes (i) to (iv) of EPA-472392. Process (iii) involves an enzymatic asymmetric ester hydrolysis of 1-acetoxy-2-(2,4-difluorophenyl-2,3-epoxypropane performed using a hydrolytic enzyme such as an esterase or a lipase in a buffer solution or in a mixture of buffer solution and an organic solvent such as diisopropyl ether, ethanol, acetone or dimethylformamide. In this process the (+)-form undergoes ester hydrolysis selectively and (+)-2-(2,4-difluorophenyl)-2,3-epoxypropanol is obtained. The (−)-1acetoxy-2-(2,4-difluorophenyl)-2,3-epoxypropane does not undergo ester hydrolysis and is recovered from the reaction liquid in high optical purity. In process (iv) the (−) -1acetoxy-2-(2,4-difluorophenyl)-2,3-epoxypropane recovered from process (iii) undergoes a normal ester hydrolysis using bases such as potassium hydroxide or sodium hydroxide and (−)-2-(2,4-difluorophenyl)-2,3-epoxypropanol is obtained.

Both the (+) and (−) forms of 2-(2,4-difluorophenyl)-2,3-epoxypropanol can be converted to (+)-2-(2,4-difluorophenyl)-1-[3-[(E) -4-(2,2,3,3-tetrafluoropropoxy)styryl]-1H-1,2,4-triazol-1-yl]-3-1H-1,2,4-triazol-1-yl) propan-2-ol involving different methods. The disadvantage of this method is that the epoxide is a reactive group which is susceptible to hydrolysis and nucleophilic attack, for example by an amino group on the enzyme. This would result in the enzyme being completely or partially deactivated.

The present inventors have found that the process can be improved by enzyme catalysed resolution of an ester or diol followed by chemical steps to the corresponding resolved epoxide.

Thus, according to a first aspect of the present invention there is provided a method of preparing an optically active compound of formula

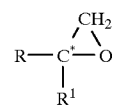

(I)

wherein R and $R^1$ are independently alkyl, alkenyl, alkynyl, alkoxy, alkoxyalkyl, cycloalkyl, aryl, aralkyl, a heterocyclic group or a $C_1$–$C_4$ alkylheterocycle, each being optionally substituted, provided that R and $R^1$ are not identical and * is an optically active chiral centre; the method comprising (a) treating a racemic compound of formula (II)

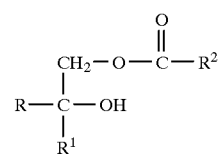

(II)

wherein R and $R^1$ are as previously defined and $R^2$ is alkyl, aryl or aralkyl each optionally substituted, with a hydrolase; or (b) treating a racemic compound of formula (III)

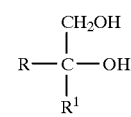

(III)

wherein R and $R^1$ are as previously defined, with a hydrolase in the presence of an acyl donor; and converting the optically active products of (a) and/or (b) to the optically active compound of formula (I).

When either of R and $R^1$ is aryl it is preferably phenyl or substituted phenyl.

When either of R and $R^1$ is aralkyl it is preferably benzyl or substituted benzyl.

When either of R or $R^1$ is cycloalkyl, it is preferably $C_{3-7}$ cycloalkyl, particularly cyclopropyl, cyclopentyl or cyclohexyl.

When either of R or $R^1$ is alkyl, alkenyl, alkynyl, alkoxy or alkoxyalkyl it preferably contains up to 10 carbons, especially 1 to 6 carbon atoms.

When either of R or $R^1$ is a heterocylic group or —$C_1$–$C_4$ alkylheterocycle, the heterocycle is preferably selected from 1,2,4-triazole, 1,3,4-triazoie, imidazole, pyrimidine, pyrazine, oxazole or pyrazole. The heterocycle may be substituted, for example, with amino, oxygen, $SO_2R^4$ or $OR_4$ where R is hydrogen, $C_{1-6}$ alkyl or phenyl. When $R^1$ is —$C_1$–$C_4$ alkylheterocycle, the alkyl group is preferably methyl or ethyl.

An especially preferred heterocycle is 1,2,4-triazole and imidazole.

Preferably, R is an optionally substituted aryl or optionally substituted aralkyl group and $R^1$ is an alkyl, alkenyl, alkynyl, alkoxy, alkoxyalkyl, cycloalkyl, aryl, aralkyl, a heterocyclic group or a $C_1$–$C_4$ alkyl-heterocycle, each being optionally substituted, provided that R and $R^1$ are not identical.

When either or both of R and $R^1$ is substituted the substituent is preferably selected from: halogen, preferably chlorine, fluorine or bromine; alkyl, preferably $C_{1-6}$ alkyl, especially methyl, ethyl, propyl, and butyl (n-, iso-, sec and tertiary forms thereof); alkoxy, preferably $C_{1-6}$ alkoxy, especially methoxy, ethoxy, propoxy and butoxy; haloalkyl, preferably $C_{1-6}$ haloalkyl especially substituted with chlorine or fluorine, particlularly trifluoromethyl and pentafluoroethyl; haloalkoxy, preferably $C_{1-6}$ haloalkoxy especially substituted with chlorine or fluorine, particularly trifluoromethoxy; cyano; nitro; amino; hydroxy; sulphonyl; and phenyl.

There may be one or more substituents and preferably when substituted there may be 1 to 3 substituents.

An especially preferred R group is phenyl substituted with one or more halogens, particularly 4-chloro, 4-fluoro, 2,4-dichloro and 2,4-difluorophenyl.

The hydrolase enzyme may be lipase, esterase, phosphatase, amidase, peptidase, suiphatase, nitrilase or glycosidase. The enzyme may be obtained from microbial culture or from plants or animals. Preferred examples of such enzymes are pig pancreatic lipase and lipase from *Chromobacterium viscosum*. Such enzymes are commercially available or can be prepared by methods known in the art.

The enzyme catalysed resolution can be carried out by any one of the following routes:

(1) hydrolytic reaction in an aqueous reaction medium;
(2) hydrolytic reaction in an aqueous medium with a miscible organic solvent;
(3) hydrolytic reaction in an aqueous/organic 2-phase reaction medium;
(4) esterification reaction in an organic reaction medium;
(5) transesterification reaction in an organic reaction medium.

It will be appreciated that because of the rtiles of nomenclature of optical forms, the designation of the configuration of the epoxide depends on the nature of the substituents about the asymmetric centre. In the general and specific examples given below the two forms of the epoxide are (R)-(+) and (S)-(−) while the two forms of the diol and ester are (R)-(−) and (S)-(+). It will be further appreciated that the system illustrated by the specific examples below can provide both configurations of the epoxide by selection of the appropriate ester or diol.

The method of the present invention when carried out by any of routes (1) to (3) is summarised by the following general reaction sequence:

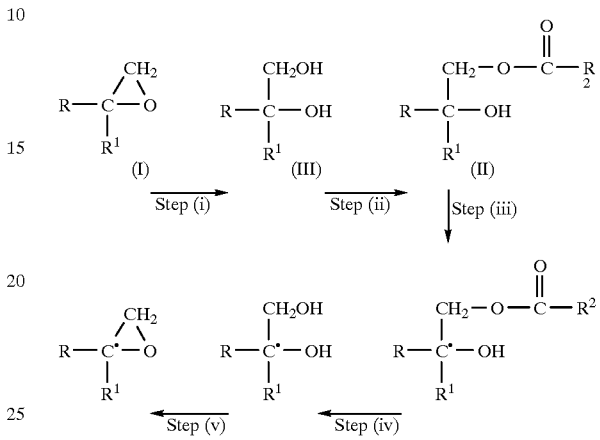

in which the compounds of formula (II) and (III) are racemic mixtures of (R)-(−) and (S)-(+) enantiomers. The racemic mixture of the compound of formula (II) is treated with a hydrolase, for example pig pancreatic lipase. The hydrolase specifically converts the undesired (S)-(+) ester to the corresponding (S)-(+) diol of formula (III). A small amount of (R)-(−) diol of formula (III) may also be formed. This conversion leaves the (R)-(−) ester of formula (II) free from the undesired (S)-(+) ester of formula (II). The (S)-(+) diol of formula (III) can be separated and either discarded, or inverted or partially inverted to give the enriched (R)-(−) diol of formula (III) or racemised to give racemic diol.

Reaction sequences (1) to (3) are more specifically illustrated by using the triazole epoxide intermediate for (+)-2-(2,4-difluorophenyl)-1-[3-[(E)-4-(2,2,3,3-tetrafluoropropoxy)styryl]-1H-1,2,4-triazol-1-yl]-3-(1H1,2,4-triazol-1-yl)propan-2-ol and 2-(2,4-difluorophenyl)-1,3-di(1,2,4-triazol-1-yl)-2-propanol (pharmaceutical fungicide, common name fluconazole):

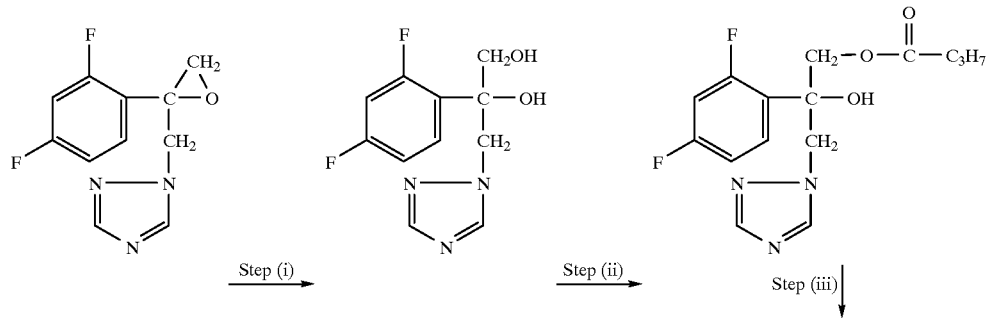

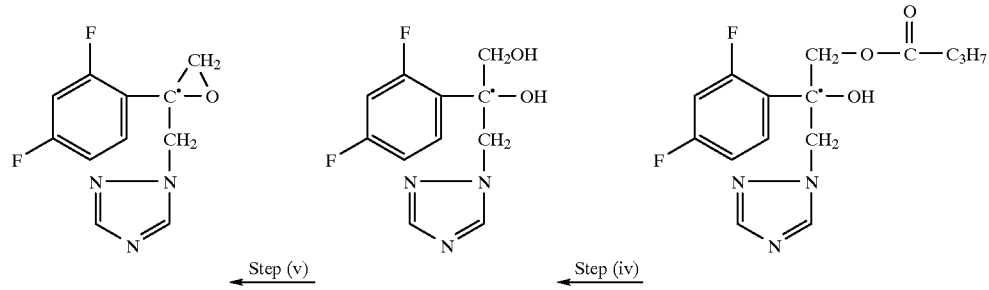

The method of the present invention when carried out by (4) and (5) is summarised by the following general reaction sequence:

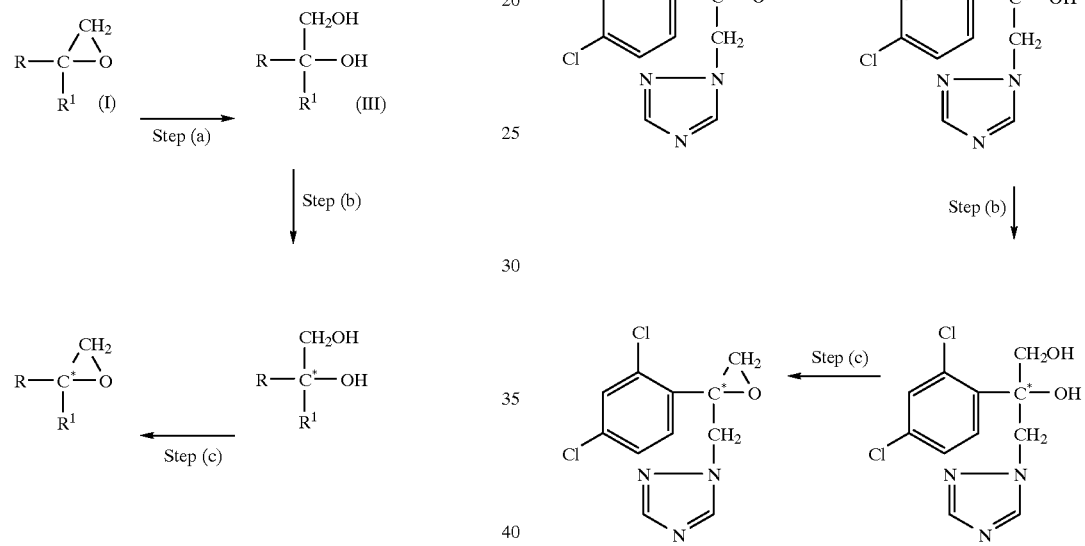

in which the compound of formula (III) is a racemic mixture of (R)-(−) and (S)-(+) enantiomers. The racemic mixture is treated with a hydrolase, for example pig pancreatic lipase, in the presence of an acyl donor, such as an alkenyl ester, for example vinyl acylate, particularly vinyl acetate, vinyl propionate, vinyl butyrate or vinyl benzoate, or such as isopropenyl acetate or isopropenyl butyrate, or an alkyl ester such as ethyl acetate or an acid of the formula $RCO_2H$ where R is alkyl, preferably $C_{1-6}$ alkyl, for example, acetic acid, propanoic acid and butyric acid.

The hydrolase specifically converts the undesired (S)-(+) diol to the corresponding (S)-(+) ester of formula (II). A small amount of (R)-(−) ester of formula (II) may also be formed. This conversion leaves the (R)-(−) diol of formula (III) free from the undesired (S)-(+) diol of formula (III). The ester of formula (II) can be separated and either discarded, or hydrolysed and inverted or partially inverted or racemised to give the (R)-(−) diol or racemic diol of formula (II).

Reaction sequences (4) and (5) are more specifically illustrated using the triazole epoxide intermediate for 2-(2, 4-dichlorophenyl)-1-(1H-1,2,4 -triazol-1-yl]-hexan-2-ol (agricultural fungicide, common name hexaconazole):

Thus, the enzyme catalysed reaction can be operated in both the hydrolytic direction as described above and also in the esterification direction by reacting the racemic diol of formula (III) with an acyl donor, such as an alkenyl ester, for example vinyl acylate, vinyl acetate, vinyl propionate, vinyl butyrate or vinyl benzoate, or such as isopropenyl acetate or isopropenyl butyrate, or an alkyl ester such as ethyl acetate or an acid of formula $RCO_2H$ where R is alkyl preferably $C_{1-6}$ alkyl, for example, acetic acid, propanoic acid, butyric acid, in the presence of a hydrolase enzyme. This transesterification route provides the ester and diol of the opposite configuration to that obtained when that same enzyme is used to catalyse the reaction by the hydrolytic route.

In all the reactions described above it is possible to recycle the unwanted enantiomer to give much greater yields and thereby gain significant economic advantages. In the hydrolytic reactions the (S)-diol is recycled to the racemic diol and in the transesterification reactions the (S)-ester is recycled to the racemic diol.

The (S)-ester may be recycled by adding an aqueous base such as sodium hydroxide to hydrolyse the (S)-ester to (S)-diol. Optionally the diol may be isolated at this stage by cooling the solution to crystallise out the product or may be kept in solution in aqueous base. In both cases the (S)-diol may be reacted with an optionally substituted aryl or alkyl sulfonyl halide, for example p-toluene sulfonyl chloride, p-nitrophenyl sulphonyl chloride, p-bromophenyl sulfonyl chloride, methansulfonyl chloride or trifluoromethansulfonyl chloride, optionally in the presence of a phase transfer catalyst which is preferably an alkylammonium salt such as tetrabutylammonium bromide. The product of the reaction is the compound of formula (I) which is substantially the (S)-enantiomer. The product is formed via an intermediate sulfone which may be optionally isolated depending on the concentration of the aqueous base used.

The (S)-epoxide (formula (S)-(I)) is hydrolysed with an aqueous acid at a temperature of between 0 and 100° C., preferably 10° C. to 80° C. and especially from 20° C. to 70° C. The product is the diol of formula (III) composed of mixtures of (R) and (S) enantiomers, the ratio of which depends on the concentration of aqueous acid used, the temperature of the hydrolysis reaction and the reaction time. For example, at a temperature of 25° C. and a reaction time of 24 hours using 1.5M sulfuric acid the percentage of (R) to (S) enantiomers in the product was 73.5% and 26.5% respectively. At a temperature of 65° C. and reaction time of 20 minutes using 8.3M sulfuric acid the percentage of (R) to (S) enantiomers in the product was 53% and 47% respectively.

The racemic diol may be isolated by basidifying the acidic solution, extracting the diol into an organic solvent such as toluene and crystallising the diol by concentrating and cooling the solution.

The (S)-diol may be recycled by reacting with an aryl or alkyl sulphonyl halide such as p-toluenesulfonyl chloride, p-nitrophenyl-sulfonyl chloride, p-bromophenylsulfonyl chloride, methansulfonyl chloride or trifluoromethansulfonyl chloride, in a solvent such as toluene, xylene, benzene, pyridine, methylisobutylketone or tetrahydrofuran with a base such as an alkylamine, preferably triethylamine or pyridine or N,N-dimethylaminopyridine or an aqueous base such as sodium or potassium hydroxide. Depending on the stoichiometry of base used the (S)-1-sulfonylester may be formed or with excess base the (S)-epoxide of formula (I). Preferably excess base is used and the (S)-epoxide is formed. When aqueous sodium hydroxide is used as a base a phase transfer catalyst such as tetrabutylammonium bromide may be used to accelerate the reaction. Suitable temperatures are between −5° C. and 50° C. preferably 20° C. to 45° C., and reaction times of 0.25 to 24 hours, preferably 0.5 to 1 hour. The (S)-epoxide is then treated as previously described for the (S)-epoxide from the recycling of the (S)-ester.

The general conditions for the enzyme catalysed reactions (1) to (3) are conventional. The enzymes are commercially available and used in the reaction mixture as received with no further treatment or the enzymes can be prior treated by dissolving in buffer at around pH7 to 7.5 and adsorbing to a support, for example, passively adsorbing to glass beads, sand, diatomateous earths (e.g. Celite®), charcoal, alumina ($Al_2O_3$), silica gel, kieselguhr or resins, e.g. Amberlite®, Dowex®, XAD® resins. Alternately the enzymes can be covalently adsorbed to a support, for example, polystyrene, epoxy resins such as Eupergit®, plastic supports. ® indicates a trademark or tradename. The adsorbed enzyme may be dried by lyophilisation (freeze-drying) of the water and then ground to a homogenous powder.

A suitable buffer is used to maintain an appropriate pH, preferably pH 5 to 9, especially pH 7.5. An aqueous base such as sodium or potassium hydroxide may optionally be added to maintain the desired pH. The reaction mixture must be stirred. The temperature of the reaction mixture is suitably from 15° C. to 35° C. and preferably from 30° C. to 35° C.

The solvent for the hydrolytic reaction is water, preferably with a miscible co-solvent such as an alcohol, preferably methanol or ethanol, or an amide, preferably dimethyl formamide, or dimethyl acetamide or a sulphoxide, preferably dimethylsulphoxide, or a nitrile, preferably acetonitrile, or an ether, preferably tetrahydrofuran or 1,4-dioxan or a ketone, preferably acetone or 2-butanone. Alternately an immiscible co-solvent may be used, for example, an arene, preferably toluene, xylene or benzene, an ether preferably t-butylmethyl ether or diethylether or a ketone, preferably 2-pentanone, 3-pentanone, 2-hexanone or 3-hexanone. In a further alternative, mixtures of water miscible and immiscible solvents may be used preferably toluene and methanol, xylene and ethanol, t-butyimethylether and methanol, 2-pentanone and acetone. An especially preferred mixture of solvents is water, methanol and toluene. The amount of miscible co-solvent is small enough to maintain both the active enzyme and a biphasic mixture but is large enough to solubilise the reactant ester.

Solvents for the transesterification reaction are suitably tetrahydrofuran, tertiary-butanol or short chain ketones such as methyl isopropyl ketone, methyl ethyl ketone (2-butanone), methyl propyl ketone (2-pentanone), methylisobutyl ketone, or toluene or a vinylacylate, e.g. vinyl acetate.

For the transesterification reaction the solvent is preferably anhydrous, i.e the solvent contains 0.5% or less water, preferably 0.1% or less water, especially 0.05% or less water (% by weight).

In situations where there is 0.5% or less water in the solvent it is known in the art to buffer the solvent at a particular activity of water which is less than that at 0.5% water by adding a hydrated or anhydrous salt or mixtures thereof. The effect is to maintain a lower activity of the water in the solvent.

It is preferable to pass nitrogen gas through the transesterification reaction system (step b) which leads to a 3 fold increase in the reaction rate. This means the reaction time is decreased or that less enzyme can be used, for example it has been demonstrated that 25% less enzyme can be used. This represents a significant economic advantage. Thus, in a preferred aspect of the present invention there is provided a method according as previously described above wherein the diol of formula (III) is treated with a hydrolase in the presence of a flow of nitrogen containing gas.

Although the transesterification reaction can be carried out at relatively low temperatures, for example 30° C., it has been found advantageous to raise the temperature to 50° C. to 80° C., preferably 60° C., to 75° C., especially 65° C. to 70° C. Thus the transesterification reaction may be carried out at temperatures ranging from 30° C. to 80° C.

When the transesterification reaction has run to completion (i.e. the (R)-diol is of high optical purity) the (R)-diol may be conveniently isolated by filtering off the enzyme and either concentrating the organic solution and seeding with (R)-diol to selectively crystallise the (R)-diol from the mixture or by removing the organic solvent and triturating the resultant oil with a different organic solvent, preferably dichloromethane, from which the (R)-diol crystallises out from the mixture. The optical purity of the (R)-diol may be enhanced during this process.

Solvents for the extraction of the product of the enzyme catalysed hydrolytic reaction routes (1–3) include any aqueous immiscible solvent, for example, alkane such as hexane or octane, ether or ketone solvents such as tertiary-butyl methyl ether, 2-hexanone, diethyl ether, pentanone or methyl isobutyl ketone, arene solvents such as toluene, xylene or benzene. Particularly preferred solvents are toluene and methylisobutylketone.

Further, recrystallisation of the product from organic solvents such as ethyl acetate, ether, hexane, dichloromethane or solvent mixtures thereof, results in the optically pure substance. Especially preferred is dichloromethane since this solvent enhances the optical purity of the product particularly from the transesterification reaction, i.e. it is possible to obtain 99.9% enantiomeric excess using this solvent.

The racemic form of the triazole epoxide can be prepared by the methods described in EP 44605 which involve reacting the corresponding ketone with trimethyloxosulphonium iodide (Corey and Chaykovsky, JACS, 1965, 87, 1353–1364) or trimethylsulphonium iodide (Corey and Chaykovsky, JACS, 84,3782) using methods set out in the literature. The ketone can be made by methods set out in the patent literature, more particularly in British Patent Specifications Nos. 1533705 and 1533706.

The racemic epoxide of formula (I) can be hydrolysed with dilute acid, for example sulphuric acid, to produce the racemic diol of formula (III). Treatment of the racemic diol of formula (III) with an acid chloride results in the esterification of the primary alcohol to yield the corresponding racemic ester of formula (II).

The racemic and enantiomeric forms of the triazole substituted ester of the present invention are novel, thus according to a further aspect of the present invention there is provided a compound of formula:

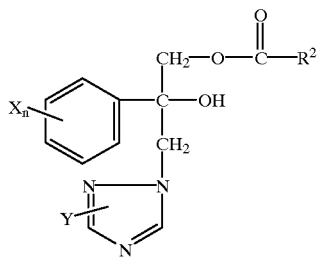

and enantiomeric forms thereof, wherein $R^2$ is alkyl or aryl, both optionally substituted, X is halogen, alkyl, haloalkyl, alkoxy, haloalkoxy, cyano, nitro, amino, hydroxy, sulphonyl or phenyl; and n is 0 to 5.

Preferably $R^2$ is $C_{1-6}$ alkyl, especially methyl, ethyl, propyl and butyl, (n-, iso-, sec- and tertiary forms thereof).

When X is halogen it is preferably chlorine, fluorine, bromine.

When X is $C_{1-6}$ alkyl, it is especially methyl, ethyl, propyl or butyl, (n-, iso-, sec- and tertiary forms thereof); or $C_{1-6}$ alkoxy, it is especially methoxy, ethoxy, propoxy and butoxy; or $C_{1-6}$ haloalkyl, the halogen is preferably chlorine or fluorine and is especially trifluoromethyl or pentafluoroethyl; or $C_{1-6}$ haloalkoxy, the halogen is preferably chlorine or fluorine and is especially trifluoromethoxy.

n is preferably 0 to 3.

The enantiomeric epoxide intermediates of the present invention are useful intermediates particularly in the preparation of agrochemicals and pharmaceuticals.

For example, the (R)-(−) diol of formula (III) where R is 2,4-difluorophenyl and $R^1$ is —$CH_2$-1,2,4-triazole can be converted to the corresponding (R)-(+) epoxide of formula (I) by the method of process 6 in EPA-472392.

The (R)-(+) epoxide of formula (I) when R is 2,4-difluorophenyl and $R^1$ is —$CH_2$-1,2,4-triazole can be used to make (+)-2-(2,4-difluorophenyl)-1-[3-[(E)-4-(2,2,3,3-tetrafluoro-propoxy)styryl]-1H- 1,2,4-triazol-1-yl]-3-(1H-1,2,4-triazol-1-yl)propan-2-ol according to the method of process 7 disclosed in EPA-472392.

Thus, in a further aspect of the present invention there is provided a method for preparation of compounds of formula V:

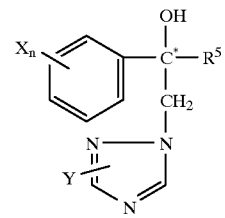

(V)

wherein $R^1$ is any of the groups previously defined for R, Y is an optional substituent, X is halogen and n is 0 to 3, which comprises the steps of: (i) preparing a compound of formula (IV):

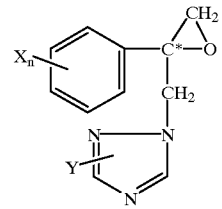

(IV)

by (a) treating a compound of formula

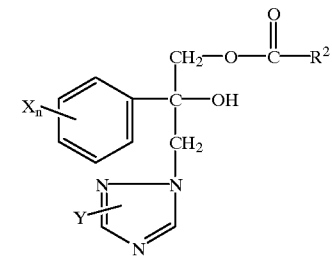

with a hydrolase; or (b) treating a compound of formula

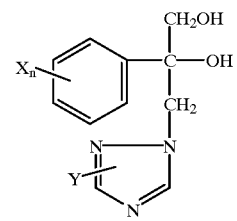

with a hydrolase in the presence of an acyl donor; (c) converting the optically active products of (a) and (b) to the optically active epoxide of formula (IV); (ii) converting the optically active epoxide of formula (IV) to the optically active compound of formula (V) in an organic solvent such as tetrahydrofuran, dimethylformamide or ethanol, in the presence of a base such as potassium carbonate, potassium bicarbonate or sodium hydride.

$R^5$ is preferably alkyl, aryl, heterocycle or alkylheterocycle as defined above for R and $R^1$, X is preferably chlorine or fluorine and Y is an optional substituent. Of particular interest are the compounds where X is 2,4-difluoro, 2,4-dichloro, 4-chloro and 4-fluoro, $R^5$ is $C_{1-4}$ alkyl, phenyl or halophenyl (particularly 2,4-difluoro, 2,4-dichloro, 4-chloro and 4-fluoro phenyl), 1,2,4-triazole or —$CH_2$-1,2,4-triazole each optionally substituted as previously defined and Y is an optional substituent which may be the same as defined above for R or may be more complex such as the 2,2,3,3-tetrafluoro-propoxy)styryl substituent mentioned above.

The invention is further illustrated by reference to the following examples which do not limit the scope of the invention.

EXAMPLE 1

Preparation of (R)-(−)-2-hydroxy-2-(2,4-difluorophenyl)-3-(1H-1,2,4-triazol-1-yl) propylbutyrate by hydrolytic resolution of the corresponding racemic ester in an aqueous reaction medium Tris-hydrochloride buffer (10 mM, pH7.2, 8.334 litres) was placed in a glass reactor and heated to 35° C. with stirring. To this was added pig pancreatic lipase (5 g, Biocatalysts, Treforest, UK) and the pH adjusted to pH 7.2 using sodium hydroxide (2M).

The corresponding racemic ester of formula (I) where $R^2=C_3H_7$ (140 g) was dissolved in methanol (1.666 litres). The reaction was started by addition of methanol solution to the aqueous enzyme solution.

The substrate was added by pumping at a rate of 67 ml/minute. The reaction pH was monitored and automatically adjusted to pH 7.2 by titration with sodium hydroxide (2M).

After 3 hours the reaction had ceased, no further titration was observed. The reaction mixture was extracted twice with 2.5 liters of toluene. The toluene was dried with anhydrous sodium sulphate and the toluene removed by vacuum distillation. The residual aqueous phase was extracted twice with 2.5 liters of ethyl acetate, dried with anhydrous sodium sulphate and the solvent removed by vacuum distillation.

The reaction was monitored by chiral stationary phase HPLC under the following conditions:
 column: Chiralcel O.D. (250 mm×4.6 mm)
 eluant: hexane:2-propanol (87.5:12.5)
 flow rate: 0.6 ml/minute
 detector: UV absorbance (205 nm)
 retention times: (S)-(+)-ester—20 minutes
  : (R)-(−)- ester—24 minutes
  : (R)-(−)- diol—28 minutes
  : (S)-(+)- diol—36 minutes The combined toluene extracts yielded 58.7 g of an oil of the following composition: (R)-(−) ester—58.01 g
 : (S)-(+) ester—not detectable
 : (S)-(+) diol—0.69 g
 : (R)-(−) diol—not detectable

EXAMPLE 2

Preparation of (R)-(−)-2-hydroxy-2-(2,4-difluorophenyl-3-(1H-1,2,4-triazol-1-yl) propylbutyrate in an aqueous/organic 2-phase reaction mixture The corresponding racemic ester of formula (I) where $R^2=C_3H_7$ (44 kg) was dissolved in a mixture of methanol (25 liters) and toluene (125 liters) by heating to 60° C. The solution was then cooled to 35° C.

Aqueous potassium phosphate buffer (50 m M, pH 7.5, 260 liters) was charged to the reactor and heated to 35±1° C. To this was added pig pancreatic lipase (1.5 kg, previously dissolved in 10 liters of phosphate buffer, pH 7.5) and the reactor stirred. Toluene (50 liters was then added to the reactor and the reaction was initiated by pumping the toluene/methanol mixture into the aqueous enzyme solution at a rate of 3.3 liters/minute. The reaction mixture was maintained at pH 7.5±0.2 by the addition of 1 molar sodium hydroxide. The reaction was monitored by chiral stationary phase HPLC under the conditions described in Example 1.

The reaction was complete after 4.5 hours (indicated by the residual (S)-(+)- ester being present at less than 1%). Celite (5 kg) was stirred into the reaction mixture and the reaction mixture was passed through a filter cloth to remove protein and aid phase separation. The aqueous and organic layers were separated. The organic layer was washed three times with 1000 liters of warm (35° C.) water to remove any diol. The final organic solution contained only (R)-(−)-ester, the yield being 15 kg and 98% enantiomeric excess.

The aqueous phase was extracted three times with ethyl acetate (65 liters ). The combined ethyl acetate extracts contained 15 kg of (S)-(+)-diol of 80% enantiomeric excess.

This example was repeated using pig pancreatic lipase or lipolase (obtained from Novo Industri) as the enzyme. The ester (100 mg) was dissolved in 7.5 ml of t-butyl methyl ether and reacted with the enzyme in 30 ml of aqueous buffer as described above. The results are presented in Table I.

TABLE I

| Enzyme | Enantiomeric excess of (R)-(−)-diol (%) |
|---|---|
| pig pancreatic lipase | 96 |
| lipolase | 20 |

EXAMPLE 3

Preparation of (R)-(−)-2-(2,4-difluorophenyl)-3-(1H-1,2,4-triazol-1-yl)propan-1,2-diol by hydrolase catalysed transesterfication in various organic solvents The reaction mixtures consisted of the corresponding racemic diol of formula (III), 25 mg; enzyme, 5 mg; and solvent 2 ml. The reactants formed a slurry in the solvent due to the insolubility of the enzyme and the partial solubility of the diol substrate. The reaction mixtures were incubated with shaking at 37° C. for 16 hours. Enzyme was removed by filtration through a membrane filter (0.2 micron diameter pores). Where the substrate or product was incompletely soluble in the reaction solvent, methanol (0.25 ml) was added to the mixture prior to filtration. This resulted in a clear solution from which the suspended enzmye could be removed by filtration. Filtrates were analysed by HPLC as described in Example 1.

Table II shows the results of the transesterification reaction with a range of lipases using vinyl butyrate as the solvent and acyl donor.

TABLE II

| Enzyme | Enantiomeric excess of (R)-(−)-diol (%) |
|---|---|
| *Chromobacterium viscosum* | 94 |
| Pig pancreatic lipase | 51 |

The method of Example 3 was repeated using various solvents and the enzyme *Chromobacterium viscosum* lipase. The reaction mixture contained: solvent 2 ml, vinyl butyrate 0.1 ml, diol 25 mg, enzyme 5 mg. The reaction mixture was incubated with shaking at 37° C. for 16 hours. The results are presented in Table III.

TABLE III

| Solvent | Enantiomeric excess of (R)-(−)-diol (%) |
|---|---|
| 2-pentanone | 81 |
| butanone | 77 |
| tetrahydrofuran | 71 |
| tertiary-butanol | 41 |

Analytical methods for the following examples were as follows: GLC was carried out using a Hewlett Packard HP5890 and integrator with a 0.25 mm capillary, 25 mm CP.Sil-5CB (Chrompack). With a temperature/time profile of 140° C. for 2 minutes then 10° C. rise per minute to 200° C. and then held at this temperature for 5 minutes. The diol elutes at about 3.8 minutes and the ester at about 5 minutes. Reverse phase HPLC was carried out using a Hewlett Packard and integrator with an ODS 25 cm×4.6 mm ID analytical column and eluent of 47.5% acetonitrile and 52.5% water at a flow rate of 1 m./min. Detection was by ultraviolet at 260 nm. Chiral HPLC was carried out using a Hewlett Packard and integrator with a Chiralcel OD25 cm×4.6 mm ID analytical column and eluent of 10% absolute ethanol and 90% n-hexane at a flow rate of 1 ml/min. The elution times were approximately as follows: (S)-ester 14.4, (R)-ester 15.8, (R)-diol 20.7, (S)-diol 23.4 minutes.

EXAMPLE 4

1 weight equivalent of racemic diol, 2-(2,4-difluoro-phenyl)-3-(1H-1,2,4-triazol-1-yl) propan-1,2-diol was dissolved in 20 volume equivalents of methyl isobutylketone (MIBK) at 60–65° C. and the mixture was stirred. 4 volume equivalents vinyl acetate were added and then a stream of nitrogen sparged through the solution via a sintered glass lance. 0.5 weight equivalents of pig pancreatic lipase (obtained from Biocatalysts) was added in one portion. The reaction was monitored by GLC, method given above, and towards the end of reaction Chiral HPLC, method given above. The reaction was stirred for 13 hours until less than 5% (S)-diol remained. The enzyme was filtered from the hot solution using a sintered glass filter and washed with a small amount of cold MIBK. The solvent was evaporated under reduced pressure on a rotary evaporator, and the resulting oil triturated with 2 volume equivalents of dichloromethane. After cooling to 5° C. and standing for thirty minutes the white crystals of R-diol that had formed were filtered off, washed with 2 volume equivalents of cold dichloromethane and air dried. This procedure gave 0.44 weight equivalents of (R)-(−)-2-(2,4-difluorophenyl)-3-(1H-1,2,4-triazol-1-yl) propan-1,2-diol, which by Chiral HPLC gave greater than 99.5% of the (R)-enantiomer. This repesents a 42% conversion. The filtrate contained 0.8 weight equivalents of a mixture containing 75% (S)-ester, 7.5% (R)-ester, 7.4% (R)-Diol and 8.1% (S)-Diol.

EXAMPLE 5

1 weight equivalent of racemic diol (formula III) was dissolved in 5 volume equivalents of MIBK at 70° C. Nitrogen was sparged through the solution and 2.5 volume equivalents vinyl acetate were added, followed by 0.25 weight equivalents of pig pancreatic lipase (obtained from Biocatalysts). The mixture was stirred at 70° C. for 6–7 hours or until <5% (S)-diol remained by chiral HPLC. The solution was filtered hot and washed with 2 volume equivalents of warm MIBK. The solution was concentrated to one-third volume and added dichloromethane and seeded with (R)-diol. The crystals were filtered off and air dried. This prodedure yielded 0.44 weight equivalents of materials of greater than 99.5% (R)-diol and greater than 85–90% strength (dichloromethane was found to be approximately 10–15% of the crystal mass).

EXAMPLE 6

The method of Example 4 was followed using 20 volume equivalents of toluene in which the racemic diol is only partially soluble, and 1 weight equivalents of pig pancreatic lipase. The reaction was stirred for 4.5 hours during which 47% of the racemic diol was converted (S)-ester.

EXAMPLE 7

The method of Example 4 was followed using 20 volume equivalents of tertiary butanol and 1 weight equivalent of pig pancreatic lipase. The reaction mixture was stirred for 1.5 hours during which 32% of the racemic diol was converted to (S)-ester.

EXAMPLE 8

The method of Example 4 was followed using 4 volume equivalents of vinyl butyrate. After 13 hours 52% of the racemic diol had been converted to the (S)-butyl ester.

EXAMPLE 9

The method of Example 4 was followed using 1 equivalent of pig pancreatic lipase. After 2.5 hours 50.6% of the racemic diol had been converted to (S)-ester.

EXAMPLE 10

The method of Example 9 was followed omitting the nitrogen stream. After 4 hours 41.5% of the racemic diol had been converted to (S)-ester.

EXAMPLE 11

The method of Example 4 was followed using 10 volume equivalents of methylisobutylketone and 4 volume equivalents of vinyl acetate. After 23 hours 47% of the racemic diol had been converted to (S)-ester.

EXAMPLE 12

The method of Example 11 was followed using a temperature of 80° C. After 4.5 hours 51% of the racemic diol had been converted to (S)-ester. The (R)-diol was isolated as described in Example 4 in 40% yield with greater than 97% enantiomeric excess.

EXAMPLE 13

The method of Example 4 was followed using 13 volume equivalents of methylisobutylketone and 2.6 volume equivalents of vinyl acetate and 0.25 weight equivalents of anhydrous sodium sulfate. After 3.75 hours 37% of the racemic diol had been converted to (S)-ester.

EXAMPLE 14

The method of Example 4 was followed using anhydrous methylisobutylketone ($H_2O$ not measureable i.e. less than 0.05%) prepared by stirring reagent grade MIBK over calcium chloride and 1 weight equivalent of pig pancreatic lipase. After 2 hours 52.5% of the racemic diol had been converted to (S)-ester.

EXAMPLE 15

The method of Example 4 was followed using reagent grade methylisobutylketone (less than 0.5% $H_2O$) and 1 weight equivalent of pig pancreatic lipase. After 2.5 hours 52% of the racemic diol had been converted to (S)-ester.

EXAMPLE 16

The method of Example 4 was followed adding 0.1 weight % water to the anhydrous methylisobutylketone. After 3 hours 52% of the racemic diol had been converted to (S)-ester.

EXAMPLE 17

The method of Example 4 was followed adding 0.5 weights % water to the anhydrous methylisobutylketone. After 5 hours 47.7% of the racemic diol had been converted to (S)-ester.

EXAMPLE 18

The method of Example 4 was followed adding 2 weight % water to the anhydrous methylisobutylketone. After 3.5 hours 11.4% of the racemic diol had been converted to (S)-ester.

EXAMPLE 19

The method of Example 4 was followed using 1 weight equivalent of pig pancreatic iipase supported on 15 weight equivalents of inert support (see Table IV). The supported lipase was prepared by dissolving 1 weight equivalent enzyme in 20 weight equivalents 50 mM potassium phosphate buffer pH 7.5 and adding 15 weight equivalents inert support. The suspensions were frozen at −78° C. and lyophilised at ambient temperature and 0.5 mm Hg pressure over 2 days. The resulting dry solid was ground to homogeneity and used directly in the reaction.

TABLE IV

| Inert Support | Time (Hrs) | % Conversion racemic diol | Relative activity of recycle catalyst |
|---|---|---|---|
| Fine glass beads | 2.5 | 10 | — |
| Fine washed sand | 4.0 | 53 | 56 |
| Celitite | 2.75 | 53 | 80 |
| Neutral Alumina | 2.5 | 33 | 33 |
| None | 2.5 | 51 | 26 |

EXAMPLE 20

The method of Example 4 was followed using 1 weight equivalent of pig pancreatic lipase supported on 0.05 weight equivalents of Eupergit (TM). The supported lipase was prepared by dissolving 1 weight equivalent enzyme in 2.5 volume equivalents 50 mM potassium phosphate buffer pH 7.5 and adding 0.05 weight equivalents Eupergit and stirring at ambient temperature for 72 hours. The solid was then filtered off and freeze dried as described in Example 19. The resulting dry solid was used directly in the reaction. After 2.5 hours 28% of the racemic diol had been converted to (S)-ester.

EXAMPLE 21

Synthesis of racemic (±)-2-(2,4-difluorophenyl)-3-(1H-1,2,4-triazol-1-yl)propan-1,2-diol by recycle of (S)-ester 1 weight equivalent of (S)-2-hydroxy-2-(2,4-difluorophenyl)-3-(1H-1,2,4-triazol-1-yl)propyl acetate was dissolved in 9 volume equivalents of toluene at 80° C. 4 volume equivalents of 100 TW caustic was added dropwise and the mixture stirred vigorously for 1 hour or until all the ester had been hydrolysed to diol as monitored by sampling from the organic phase by GLC. The mixture was cooled to 25° C. and 0.7 weight equivalents p-toluene sulfonyl chloride in 4 volume equivalents of toluene, with 0.2 weight equivalents of tetrabutyl ammonium bromide were added and the mixture stirred vigorously at ambient temperature until all the diol was converted to epoxide by GLC monitoring of the organic phase. The aqueous phase was separated and the toluene solution warmed to 60° C. 0.9 volume equivalents of 45% sulphuric acid was added dropwise and stirred for 30 minutes. The reaction mixture was cooled to 25° C. the organic layer was separated and the aqueous layer basified by addition of 50 volume equivalents of 1M caustic to pH9. To this solution 9 volume equivalents of MIBK were added. The solution was warmed to 65° C. and stirred then the aqueous layer salted with sodium chloride, stirred and separated. The MIBK solution was cooled and racemic diol crystallised out. The crystals were filtered, washed with cold MIBK and air dried. This procedure gave 0.68 weight equivalents of diol, which by chiral HPLC was found to be between 5–10% enantiomeric excess of (R)-diol.

EXAMPLE 22

Recycle of S-(−)-diol to racemic diol

S-(+)-diol (1 equivalent) and p-toluene sulfonyl chloride (1 equivalent) are slurried together in 4 volume equivalents of toluene and stirred. 4M sodium hydroxide (2.5 volume equivalents) was added as drops over 30 minutes at ambient temperature. The reaction mixture was allowed to warm to 40° C. which was held for 30 minutes. The toluene layer was separated while the remaining aqueous layer was rewashed with a further 1 volume equivalent of toluene. The toluene extracts were combined and added slowly over 10 minutes to a solution of 45% (V:V) sulfuric acid (0.3 volume equivalents) at 65° C. This temperature was held for a further 10 minutes and then cooled to 25° C. and basidified to pH 9 using 100 Tw sodium hydroxide. 3 volume equivalents of water were added and the diol extracted from the aqueous solution by washing 3 times with 4 volume equivalents of ethyl acetate. The extracts were combined and the solvent removed under reduced pressure at 50° C. The product yielded 0.75 equivalents of diol 53% (R)-enantiomer and 47% (S)-enantiomer.

EXAMPLE 23

Recycle of S(+)-diol to enriched (R)-diol

S(+)-diol (1 equivalent), p-toluene sulfonyl chloride (1.1 equivalents) and tetrabutylammonium bromide (0.031 equivalents) were slurried together in 4 volume equivalents of toluene at ambient temperature. The mixture was stirred vigorously and a solution of 4M sodium hydroxide (2.5 volume equivalents was added over 30 minutes. The solution was stirred a further 45 minutes until all the S(+)-diol had reacted. The total reaction mixture was screened and the filter cake washed with toluene (0.5 volume equivalents). The lower aqueous phase from the filtrate was separated off and diluted with water (4 volume equivalents) then rewashed with 1.5 volume equivalents of toluene that has been used to wash the filter cake. This solution is then refiltered through celite to allow separation of the phases. The toluene layer is separated and all toluene fractions combined and then re-washed with water. The toluene layer is separated and the volume reduced to 3.5 volume equivalents. Sulfuric acid (1.5M, 2.25 volume equivalents) at 25° C. is added to the toluene solution over 1 hour at 25° C. and stirred for 24 hours. The reaction mixture was then heated to 65° C. for 2 hours, then cooled to room temperature. The aqueous layer was separated and the organic layer discarded. The aqueous layer was basified with 100 Tw sodium hydroxide and the solution cooled to 10° C. from which the diol crystallised out, was filtered off and air dried. 0.79 equivalents of diol were recovered which corresponded to 73.5% of R-diol and 26.5% of S-diol.

We claim:

1. A compound of the formula: to:

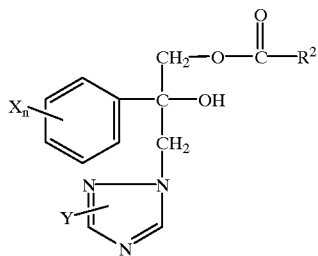

and enantiomeric forms thereof, wherein $R^2$ is alkyl; X is halogen, alkyl, haloalkyl, alkoxy, haloalkoxy, cyano, nitro, amino, hydroxy, sulphonyl or phenyl; n is 0 to 5; and Y is optionally halogen, alkyl, alkoxy, haloalkyl, haloalkoxy, cyano, nitro, amino, hydroxy, sulphonyl, phenyl or 2,2,3,3-tetrafluoropropoxy-styryl.

2. The compound of claim 1, wherein $R^2$ represents a $C_{1-6}$ alkyl group.

3. The compound of claim 1, wherein X represents F, Cl, Br, $C_{1-6}$ alkyl, $C_{1-6}$ alkoxy, $C_{1-6}$ haloalkyl or $C_{1-6}$ haloalkoxy.

4. The compound of claim 3, wherein X represents F or Cl.

5. The compound of claim 1, wherein the triazole ring is unsubstituted.

6. The compound of any one of claims 1–5, wherein n is 0–3.

7. The compound of claim 1, wherein $R^2$ represents a $C_{1-6}$ alkyl group and X represents F, Cl, Br, $C_{1-6}$ alkyl, $C_{1-6}$ alkoxy, $C_{1-6}$ haloalkyl or $C_{1-6}$ haloalkoxy.

8. The compound of claim 1, wherein $R^2$ represents a methyl, ethyl, n-propyl, sec-propyl, n-butyl, sec-butyl or tertiary butyl group and X represents F, Cl, trifluoromethyl, pentafluoroethyl or trifluoromethoxy.

9. The compound of claim 7 or 8 wherein X represents F or Cl.

10. The compound of claim 7 or 8 wherein X represents 2,4-difluoro or 2,4-dichloro.

* * * * *